United States Patent [19]

Godbille

[11] Patent Number: 4,613,405

[45] Date of Patent: Sep. 23, 1986

[54] APPARATUS TO CONCENTRATE SOLUTIONS AND TO RECOVER SOLVENTS

[75] Inventor: Etienne Godbille, Villemonble, France

[73] Assignee: Roussel UCLAF, Romainville, France

[21] Appl. No.: 641,202

[22] Filed: Aug. 16, 1984

Related U.S. Application Data

[63] Continuation of Ser. No. 398,620, Jul. 15, 1982, abandoned.

[30] Foreign Application Priority Data

Jul. 17, 1981 [FR] France .................................. 81 13959

[51] Int. Cl.4 .......................... B01D 1/06; B01D 1/22
[52] U.S. Cl. ..................................... 159/13.3; 159/49; 422/307; 436/174
[58] Field of Search ............... 203/49, 89, 87, DIG. 2; 202/83, 163, 176, 177, 232, 234, 236, 237; 159/5, 131, 133, 15, 49, DIG. 10, DIG. 11, DIG. 1; 436/174; 422/307

[56] References Cited

U.S. PATENT DOCUMENTS

| | | | |
|---|---|---|---|
| 2,310,399 | 2/1943 | Cox et al. | 202/205 |
| 2,530,376 | 11/1950 | Castle et al. | 202/205 |
| 3,250,687 | 5/1966 | Frank | 202/205 |

FOREIGN PATENT DOCUMENTS 1043334 11/1958 Fed. Rep. of Germany ........ 203/49

Primary Examiner—Frank Sever
Attorney, Agent, or Firm—Bacon & Thomas

[57] ABSTRACT

Apparatus to concentrate solutions and to recover solvents, comprising a column (1) equipped with a heating body (2), a distributor (3) of the liquid to be introduced and treated in the column (1); means (4) effecting simultaneously the flow of the concentrated liquid and the introduction of a flow of gas into the column (1) and means (20) to insure the maintenance of the internal temperature of the column (1).

15 Claims, 3 Drawing Figures

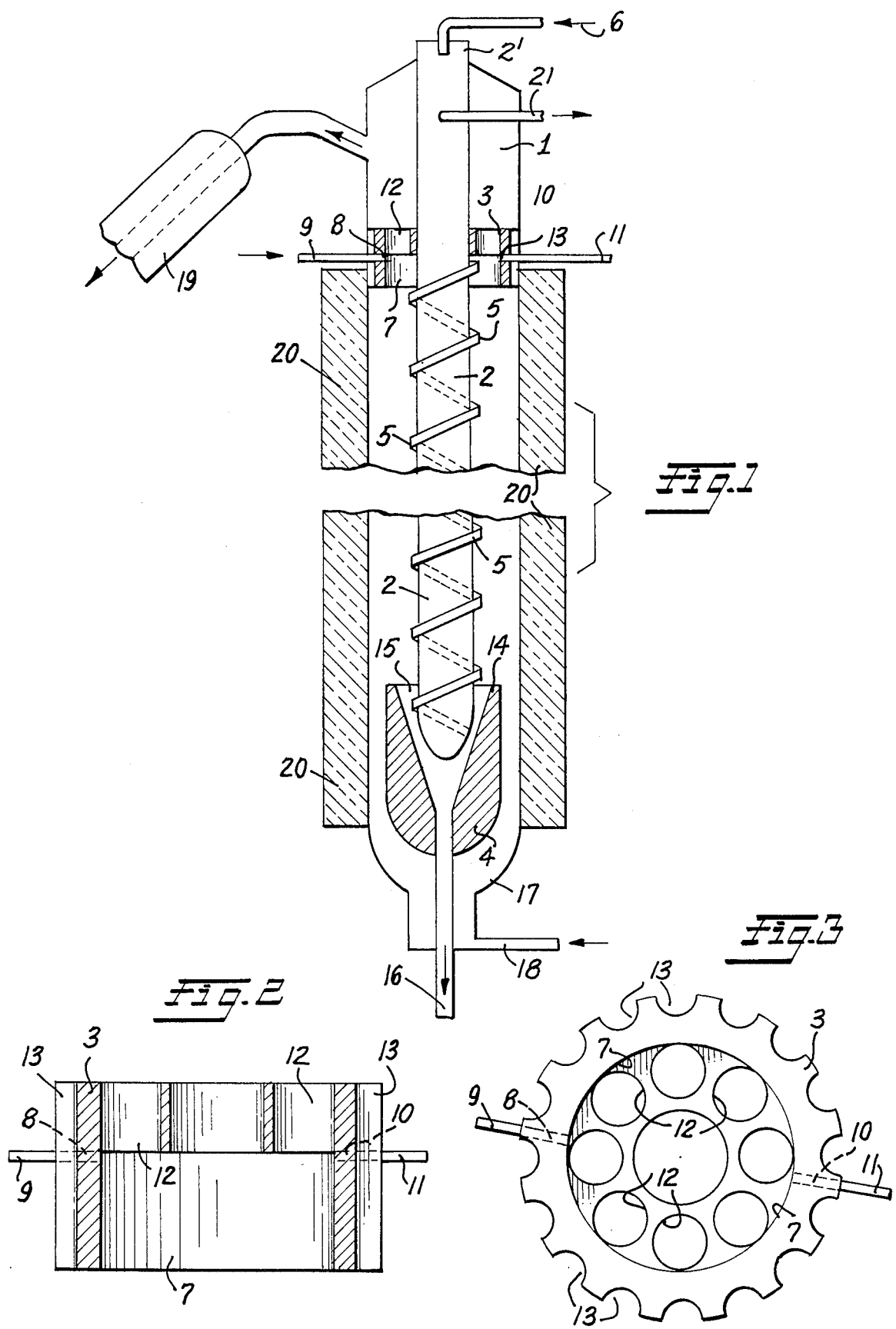

APPARATUS TO CONCENTRATE SOLUTIONS AND TO RECOVER SOLVENTS

This application is a continuation of application Ser. No. 398,620, filed July 15, 1982, now abandoned.

The object of the present invention is an apparatus and process to concentrate solutions and to recover solvents.

More particularly, it is the object of the invention to provide an apparatus and process making it possible to prevent the accumulation of large quantities of solutions by concentrating the solutions at the rate at which they are introduced into the apparatus and pass through it, and to reuse the solvent.

The apparatus of the present invention may be advantageously used during chromatography operations, particularly when these operations are on a semi-industrial or industrial scale.

An essential advantage of the apparatus of the invention comprises the fact that the volume of the liquid may be reduced in order to obtain the degree of concentration desired (between all or nothing), in a continuous manner, by means of regulating the liquid stream, in particular, as a function of the flow rate of the chromatographic column. The different products contained in the solutions issuing from the chromatographic process remain chronologically spaced apart so that it is not necessary to have recourse to the intermediate storage of the solution and the collection of the concentrates containing the different products is effected without the risk of new intermixing and contamination. This advantage is fundamental in preparative chromatography and in all other physical or chemical processes involving the flow of a fluid, the composition of which varies with time.

A further remarkable advantage consists of the fact that the evaporated solvent is recovered and may be recycled continuously to the beginning of the process, thereby appreciably reducing the volumes involved.

Finally, the concentration treatment, effected under an inert gas, retains the solution for only a few seconds at the evaporation temperature which is a highly favorable condition in the treatment of thermolabile molecules.

The drawings attached hereto illustrate the invention without limiting it.

In the drawings, the dimensions and proportions are often exaggerated in order to render the drawings clearer.

FIG. 1 shows a schematic view of the entire apparatus of the invention.

FIG. 2 shows a schematic view in cross section of the distributor (3).

FIG. 3 is a schematic bottom view in projection of the distributor (3).

The apparatus which is the object of the present invention comprises a column (1) equipped with an inlet for the liquid to be treated, a gas inlet, an outlet for the treated liquid and an outlet for the solvent vapors to be recovered. The column (1) is further equipped with a heating body (2), placed axially and heated by the circulation of a temperature control liquid inside the body, a distributor (3) of the liquid to be treated, means (4) to effect simultaneously the flow of the concentrated liquid dropping from the heating body and the introduction of a flow of gas in the column (1) and means (2) to insure the maintenance of the inside temperature of the column (1). The apparatus is further characterized by the following features:

The heating body (2) has the configuration of a finger of a glove and the active part of its surface which receives the liquid to be treated contains a plurality of flow guides (5) so as to present an optimum contact surface to the liquid to be treated and assures regular distribution of the liquid over its surface;

the distributor (3) of the liquid to be treated is in the form of an annulus, the inner diameter of which permits the passage of the inactive part (2') of the heating body (2), which is not equipped with flow guides (5);

the means (4) which simultaneously insures the flow of the liquid dropping from the heating body (2) and the introduction into the column (1) of a flow of gas is a cylindrical body (14) in the form of a sink (15).

The apparatus that is the object of the invention is also characterized by the following features:

A portion of the surface of the internal circumference of the distributor (3) is hollow, this center cavity (7) communicates through the channel (8) with the inlet conduit (9) for the liquid to be treated and through the channel (10) with a rinsing channel (11) and places the liquid to be treated in contact with the flow guides (5) and the heating body (2);

the distributor (3) is equipped either with axial channels (12) arranged in a circular manner, or with axial recesses (13) located on the external circumference of the distributor (3), or both;

the cylindrical body (14) hollowed in the form of a sink (15) is placed axially in the column (1) and the cavity in the form of a sink (15) is capable of receiving the lower end of the heating body (2);

the sink (15) extends into a conduit, the end (16) whereof passes through the part (17) closing the lower end of the column (1), with the inlet (18) for the flow of gas also being provided in said part (17).

The apparatus of the invention will become more apparent from the following embodiments:

The column (1) may be made in two or more parts in order to facilitate the assembly of the apparatus of the invention.

The materials used for the construction of the elements of the apparatus are those usually employed in distillation columns, such as glass, stainless steel, plastic materials, such as teflon, polyethylene, polypropylene or the like.

The flow guides (5) of the heating body (2) may be integral with the body or they may be applied to the heating body (2); they may consist of stainless steel, glass or a plastic material. Other types of relief favoring the flow and the distillation of the liquid to be treated may also be employed on the heating body (2).

The circulation (6) of the temperature control liquid may consist of a descending helix to lead the said liquid and of an evacuating conduit (21) to remove the cooled liquid from the column (1).

The temperature control liquid may consist of for example, water, glycol or an oil.

The means insuring the heating of the heating body (2) may also consist of an electric device or a heating circulating gas, such as water vapor or an inert gas.

The cylindrical body (4) which constitutes the means to insure the flow of the concentrated liquid from the column (1) may be held in place by retaining lugs placed in the column (1) and it may be made of glass, a plastic material or stainless steel.

The column (1) may have, depending on the dimension of the installations to which it is attached, a length of 2 to 7 meters and a diameter from 80 mm to 350 mm, for flow rates of 3 liters/hour to 150 liters/hour. Smaller or larger dimensions are also applicable.

The heating flue (20) of the column (1) may consist of a jacket equipped with a heating device such as an electric circuit, a temperature control liquid or a gas. This heating device may further be connected with the heating means of the heating body (2) and operate in series.

The flow guides (5) of the heating body (2) are placed at a more or less acute angle with respect to the axis of said heating body (2). This angle is preferably very small to reduce the flow rate of the solution along the guides and to thereby facilitate the evaporation of the solvent. By choosing a small angle of inclination of the guides (5), the number of guides (5) over a given length of the heating body will be larger and the evaporation of the solvent is further improved.

The channel (8) of the distributor and the channel (9) of the inlet conduit of the liquid to be treated may be joined by means of a connection provided for this purpose. In a variant, they may be replaced by a single channel passing through the column (1) and the distributor (3). The same is also true for the channel (10) of the distributor (3) which communicates with the rinsing channel (11).

The length of the channel (8) and of the channel (10) of the distributor (3) is advantageously chosen so that the liquid to be treated and the rinsing liquid are conducted into the proximity of the heating body (2).

In considering the drawings it may be seen that:
(1) represents the column,
(2) the heating body,
(2') the inactive part of the heating body (2) which is not equipped with flow guides,
(3) the distributor of the liquid to be treated,
(4) the means for insuring simultaneously the flow of the concentrated liquid dropping from the heating body (2) and the introduction of a flow of gas into the column (1),
(5) flow guides on the heating body in its active part intended to receive the liquid to be treated,
(6) the means in the form of the circulation of a temperature control liquid effecting the heating of the heater body,
(7) the center cavity of the distributor (3),
(8) the channel of the distributor (3) communicating with the inlet conduit (9) of the liquid to be treated,
(10) the channel of the distributor (3) communicating with the rinsing channel (11),
(12) The axial channels of the distributor (3),
(13) the axial recesses of the distributor (3)
(14) the cylindrical body in the form of which the means (4) are embodied;
(15) the sink in the form of which the cylindrical body (14) is hollowed out,
(16) the end of the conduit by which the sink is extended,
(17) the part closing off the lower end of the column (1),
(18) the inlet in the column (1) for the gas,
(19) the condenser to condense the solvent evaporated and entrained by the gaseous flow,
(20) the heating flue, and
(21) the conduit to remove the cooled temperature controlled liquid.

The apparatus according to the present invention may be used in the manner described as follows:

A solution to be concentrated and the solvent recovered are introduced by the channnels (9) and (8) into the center cavity (7) of the distributor (3). The solution may be from a chromatographic separation, for example. Once introduced in the center void (7), preferably in the proximity of the heating body, the solution enters into contact with the active part of the heating body (2), i.e. the part equipped with the flow guides (5).

Once this contact is established, the liquid commences to descend along the heating body (2) by following the flow guides (5) of the latter (2). During its descent, the solution is heated and under the combined action of the heating and the gas rising in the column (1), the solvent evaporates and is entrained by the gaseous flow introduced in the column (1) through the inlet (18), toward the top of the column (1).

When the vapors have passed through the distributor (3) by way of the axial recesses (13) and/or the axial channels (12), they travel to the condenser (19) where they are condensed and the outlet (19), where the solvent is recovered.

The concentrated solution is collected in the sink (15) and conducted through the conduit (16) to further processing.

An inert gas, such as nitrogen, is used preferentially as the gas.

The flow rate and the temperature of the gaseous flow play an important role in the evaporation of the solvent.

They depend:
on the nature of the solvent to be evaporated,
the flow rate of the liquid injected in the column,
the temperature to which the solution may be exposed, in view of the very short time during which the solution is exposed to this temperature.

As a general rule, the temperature will be controlled at a point slightly lower then the boiling point of the solvent to be evaporated and the gaseous flow is controlled so as to obtain the concentration ratio desired.

The heating flue (20) makes it possible to maintain the temperature prevailing within column (1) and thus preventing the condensation of vapors of the solvent on the walls and consequently the accumulation of the condensate formed in the lower end of the column (1) and its penetration into the inlet (18) reserved for the flow of gas.

The apparatus of the present invention is not limited to the specific embodiments described, but all variants are included.

What is claimed is:

1. An apparatus to prevent the accumulation of large quantities of solutions by concentrating the solutions at the rate at which they are introduced into the apparatus and recovering solvents continuously comprising means to prevent the accumulation of large quantities of solutions by concentrating the solutions at the rate at which they are introduced into the apparatus including a column equipped with a heating body placed axially, an inlet for the liquid solution to be treated, a distributor of the introduced solution, an outlet for the liquid treated, an inlet for a flow gas and an outlet for the solvent vapors to be recovered and a heating means insuring the maintenance of the internal temperature of said column, wherein the column comprises, a heating body containing in its active part a plurality of flow guides, a distributor of the liquid to be treated which is placed toward the upstream end of the column and which distributes both the liquid to be treated and the rinsing liquid onto the surface of the heating body and which is simultaneously permeable to the solvent vapors and flow gas, an outlet for the solvent vapors being positioned to receive said solvent vapors after said vapors pass through said distributor;

and a cylindrical body hollowed in a form of sink placed axially in the column and positioned toward the downstream end of the column for effecting simultaneously the flow of the concentrated liquid dropping from the heating body to the outlet from the liquid treated and the introduction of a flow gas into the column through the flow gas inlet.

2. An apparatus according to claim 1, wherein the heating body has the shape of a finger of a glove and its heating is insured by a heating flue.

3. An apparatus according to claim 2 wherein the distributor of the liquid to be treated is in the form of an annulus, the internal diameter of which permits the passage of the inactive part of the heating body which does not contact the liquid to be treated.

4. An apparatus according to claim 3, wherein a portion of the surface of the internal circumference of the distributor is hollow and creates a center cavity which communicates through a channel with the inlet conduit of the liquid to be treated and through a second channel with a rinsing channel allows the liquid to be treated to enter into contact with flow guides and the heating body.

5. An apparatus according to claim 2, wherein a portion of the surface of the internal circumference of the distributor is hollow and creates a center cavity which communicates through a channel with the inlet conduit of the liquid to be treated and through a second channel with a rinsing channel allows the liquid to be treated to enter into contact with flow guides and the heating body.

6. An apparatus according to claim 2 wherein the distributor is equipped either with axial channels arranged in a circular manner, or with axial recesses arranged on the external circumferences of said distributor, or with both, simultaneously.

7. An apparatus according to claim 1, wherein the heating of the heating body is effected by circulation of a temperature controlled liquid inside said heating body.

8. An apparatus according to claim 1, wherein a portion of the surface of the internal circumference of the distributor is hollow and creates a center cavity which communicates through a channel with the inlet conduit of the liquid to be treated and through a second channel with a rinsing channel allows the liquid to be treated to enter into contact with flow guides and the heating body.

9. An apparatus according to claim 1 wherein the distributor is equipped either with axial channels arranged in a circular manner, or with axial recesses arranged on the external circumferences of said distributor, or with both, simultaneously.

10. An apparatus according to claim 9 wherein the means for simultaneously effecting the flow of the concentrated liquid dropping from the heating body and the introduction into the column of the flow gas having the configuration of a cylindrical body placed axially in the column, which is hollowed in the form of a sink which has a diameter smaller than the inner diameter of the column and is capable of receiving the lower end of the heating body, said sink extending to form a conduit the end of which passes through a part closing off the lower end of the column and the inlet for the flow of gas also being provided in said part.

11. An apparatus according to claim 9 wherein the means for simultaneously effecting the flow of the concentrated liquid dropping from the heating body and the introduction into the column of the flow gas having the configuration of a cylindrical body placed axially in the column, which is hollowed in the form of a sink which has a diameter smaller than the inner diameter of the column and is capable of receiving the lower end of the heating body, said sink extending to form a conduit the end of which passes through a part closing off the lower end of the column and the inlet for the flow of gas also being provided in said part.

12. A process to concentrate a solution and to recover a solvent continuously which comprises preventing the accumulation of large quantities of solution by concentrating the solution at a rate at which they are introduced into an apparatus by, introducing a solution as a liquid to be treated in the inlet of the apparatus to concentrate solutions and to recover solvents continuously comprising a column equipped with a heating body placed axially, an inlet for the liquid solution to be treated, a distributor of the introduced solution, an outlet for the liquid treated, an inlet for a flow gas and an outlet for the solvent vapors to be recovered and a heating means insuring the maintenance of the internal temperature of said column, wherein the column comprises, a heating body containing in its active part a plurality of flow guides, a distributor of the liquid to be treated which is placed twoard the upstream end of the column and which distributes both the liquid to be treated and the rinsing liquid onto the surface of the heating body and which is simultaneously permeable to the solvent vapors and a flow gas, an outlet for the solvent vapors being positioned to receive said solvent vapors after said vapors pass through said distributor;

and a cylindrical body hollowed in a form of sink placed axially in the column and positioned toward the downstream end of the column for effecting simultaneously the flow of the concentrated liquid dropping from the heating body to the outlet from the liquid treated and the introduction of a flow gas into the column through the flow gas inlet, and continuously recovering the solvent from said solution at the outlet for the solvent vapors and collecting concentrated solution from the sink.

13. The process of claim 12, wherein the recovered solvent is returned to a chromatographic column from which the solution to be treated was obtained and introduced into the inlet of said apparatus.

14. The process of claim 12, wherein the solution to be treated is retained for only a few seconds at the evaporation temperature of the solution.

15. The process of claim 14, wherein the evaporation temperature is controlled at a temperature slightly lower than the boiling point of the solvent to be evaporated and the gaseous flow is controlled to obtain a specific concentration ratio in the concentrated solution.

* * * * *